(12) United States Patent
Urmey

(10) Patent No.: US 8,571,666 B2
(45) Date of Patent: Oct. 29, 2013

(54) NERVE STIMULATION SYSTEM WITH PROGRAMMED PULSE CHARGE ATTENUATION

(76) Inventor: William F. Urmey, Larchmont, NY (US)

( * ) Notice: Subject to any disclaimer, the term of this patent is extended or adjusted under 35 U.S.C. 154(b) by 1614 days.

(21) Appl. No.: 11/461,308

(22) Filed: Jul. 31, 2006

(65) Prior Publication Data

US 2007/0032841 A1    Feb. 8, 2007

Related U.S. Application Data

(60) Provisional application No. 60/705,009, filed on Aug. 2, 2005.

(51) Int. Cl.
*A61N 1/08* (2006.01)
*A61N 1/32* (2006.01)

(52) U.S. Cl.
USPC ............................................. 607/46; 607/47

(58) Field of Classification Search
USPC ................................................ 607/46, 47, 72
See application file for complete search history.

(56) References Cited

U.S. PATENT DOCUMENTS

| | | | |
|---|---|---|---|
| 4,453,548 A | 6/1984 | Maurer et al. | |
| 4,515,168 A | 5/1985 | Chester | |
| 4,535,777 A | 8/1985 | Castel | |
| 4,690,145 A | 9/1987 | King-Smith et al. | |
| 4,759,368 A * | 7/1988 | Spanton et al. | 607/46 |
| 5,314,457 A | 5/1994 | Jeutter et al. | |
| 6,533,732 B1 | 3/2003 | Urmey | |
| 6,671,557 B1 | 12/2003 | Gliner | |
| 6,701,190 B2 | 3/2004 | Gliner | |
| 2002/0055762 A1 | 5/2002 | Gliner | |
| 2003/0045909 A1 | 3/2003 | Gross et al. | |
| 2003/0149451 A1* | 8/2003 | Chomenky et al. | 607/3 |
| 2003/0204224 A1 | 10/2003 | Torgerson et al. | |
| 2003/0236469 A1 | 12/2003 | Hedgecock | |
| 2004/0199084 A1 | 10/2004 | Kelleher et al. | |
| 2004/0260358 A1 | 12/2004 | Vaughan | |
| 2005/0004623 A1 | 1/2005 | Miles | |
| 2005/0101878 A1 | 5/2005 | Daly et al. | |

* cited by examiner

*Primary Examiner* — Tammie K Heller
(74) *Attorney, Agent, or Firm* — Seth Natter; Natter & Natter

(57) ABSTRACT

A processor implemented nerve stimulation system for regional anesthesia administration varies pulse width as a programmed function of applied current or varies applied current as a function of adjusted pulse width. The system also provides a waveform of repeating cycles of different pulse width components separated within the waveform frequency and which may be simultaneously attenuated as a function of applied current within an attenuation range. Among possible functional relationships between pulse width and applied current within an attenuation range is the exponential reduction of pulse width as a function of applied current.

20 Claims, 4 Drawing Sheets

NERVE STIMULATION SYSTEM WITH PROGRAMMED PULSE CHARGE ATTENUATION

RELATED APPLICATIONS

This application claims the benefit of U.S. Provisional Application No. 60/705,009 filed Aug. 2, 2005.

BACKGROUND OF THE INVENTION

1. Field of the Invention

The present invention relates to nerve stimulation for regional anesthesia administration and more particularly to a processor implemented nerve stimulation system which varies pulse charge over an attenuation range by varying pulse duration as a function of applied current or applied current as a function of pulse duration.

2. Antecedents of the Invention

The field of regional anesthesia relates to the practice of administering anesthesia to a specific body region during surgery, for the relief of postoperative pain, and for extended relief of trauma or chronic pain. Often, regional anesthesia has been found to be preferable to general anesthesia because of increased safety, the availability of postoperative pain control and decreased anesthetic costs.

Regional anesthesia delivery techniques strove to optimize administration of a local anesthetic in close proximity to a target or nerve plexus so as to establish a neural blockade. Successful administration of regional anesthesia was dependent upon the accurate placement of the anesthetic in relation to the target nerve or nerves.

Various techniques have been employed to assist in placement of an administration needle in close proximity to the target nerve, which was not externally visible. One of the traditional methods of needle placement involved eliciting paresthesia. Among the disadvantages of this technique was the lack of accurate patient responses amongst patients who were disoriented and/or sedated.

A prevalent technique employed the use of nerve stimulators electrically coupled to a nerve stimulator needle. Such method was premised upon the phenomenon that an electrical pulse is capable of stimulating a motor nerve fiber to contract an innervated muscle or cause paraesthesia, in the case of sensory nerve stimulation.

The nerve stimulator needle was placed within the tissue of the patient's body in the vicinity of the nerve to be blocked and then advanced until stimulation of the target nerve was achieved as determined by visually detecting muscle contractions or by eliciting a report that the patient felt the stimulus in response to the current flow through the stimulator needle.

The current supplied by the nerve stimulator was reduced as the nerve stimulator needle was further advanced, until stimulation of the target nerve was achieved using a reduced current level associated with a prescribed distance between the needle tip and the target nerve.

Conventional electrical nerve stimulation techniques have utilized a weak direct current electrical current supplied to a nerve stimulator needle by an oscillating (square-wave) current generator. The current was pulsed, typically at a frequency of 1 Hz or 2 Hz. Current amplitude was adjusted, for example, by a potentiometer with the frequency and pulse duration remaining constant. When appropriate motor contractions, which corresponded to the muscular innervation of the targeted nerve or plexus, occurred at the set frequency, the current was slowly decreased in amperage while the needle was advanced to search for the nerve. Motor contractions that occurred at a very low amperage (usually 0.2-0.5 mAmp) indicated close proximity or contact between the needle tip and the nerve. Thereafter, a portion of the anesthetic dose was administered through the needle to terminate the response to the nerve stimulation current. If the response was terminated by the initial administration, the needle was deemed to be properly positioned in proximity to the target nerve and the remaining dose of anesthetic was administered.

Pulse duration, i.e. pulse width, is the duration in milliseconds of the periodic pulse square wave used to stimulate the nerve or nerve plexus. Increasing the pulse duration or the current amplitude increased the total flow of electrons i.e. pulse charge, in a manner proportional to the area under the square waveform. Increasing pulse duration therefore resulted in increased ability to stimulate the nerve at a greater distance which was a function of the pulse width, if other parameters, including current amplitude, are maintained constant. Greater pulse width (e.g. 0.3 msec compared to 0.1 msec) resulted in higher sensitivity to stimulate the designated nerve or plexus at a greater distance. By contrast, lower pulse width (e.g. 0.1 msec or 0.05 msec) maximized specificity for ultimate final location of the nerve relative to the needle tip. This assured optimal positioning of the needle.

The majority of nerve stimulators used have a preset single pulse duration (e.g. 0.1 msec or 0.2 msec). Some recent nerve stimulators permitted pulse duration to be set at a selected pulse width, e.g. 0.1 msec, 0.3 msec, 0.5 msec, or 1.0 msec.

A nerve stimulator that generated alternating sequential electrical pulses of high and low pulse widths was disclosed in U.S. Pat. No. 5,853,373. The high duration pulses were said to stimulate the target nerve at one-second intervals after skin penetration at a distance where the low duration pulses did not generate observable stimulation. When the target nerve was approached, both high and low duration pulses were said to generate observable stimulation (motor contractions) at one-half second intervals (twice the frequency initially observed), without a reduction in current amplitude.

SUMMARY OF THE INVENTION

A nerve stimulation system varies one nerve stimulator output component, e.g. pulse width or pulse amplitude, as a function of the operator set incremental value of the other component.

The nerve stimulation system includes a controller coupled to a display as well as operator input devices, such as keys, switches, a touch screen, a potentiometer, etc. The controller generates a signal for actuation of pulse generation hardware, which generates a pulse wave current output.

The controller is programmed to vary, for example, pulse width, as a function of the operator adjusted incrementally set value of pulse current amplitude. The function is not necessarily linear and is selected to optimally generate a linear relationship between stepped incremental values of current amplitude and the distance between the nerve stimulation needle tip and the target nerve.

The controller may be set in a mode for generation of a pulse waveform having repeating cycles of different pulse width components, with each pulse width component individually varying as a function of the operator adjusted incrementally set value of pulse amplitude.

From the foregoing compendium, it will be appreciated that it is an aspect of the present invention to provide a nerve stimulation system of the general character described which increases efficiency in the administration of regional anesthesia.

A feature of the present invention is to provide a nerve stimulation system of the general character described which simplifies the administration of neural blockade anesthesia.

A consideration of the present invention is to provide a nerve stimulation system of the general character described which is relatively simple to use.

Another aspect of the present invention is to provide a nerve stimulation system of the general character described, which facilitates guidance of a nerve stimulation needle.

Another consideration of the present invention is to provide a nerve stimulation system of the general character described which is well suited for low cost mass production fabrication.

A still further aspect of the present invention is to provide a nerve stimulation system of the general character described which varies pulse charge as a transfer function of an operated adjusted incrementally set value of a pulse charge parameter.

Another feature of the present invention is to provide a nerve stimulation system of the general character described which generates cycles of different pulse width components, with each component individually varying as a transfer function of an operator adjusted incrementally set value of pulse amplitude.

Other aspects, features and considerations of the present invention in part will be obvious and in part will be pointed out hereinafter.

With these ends in view, the invention finds embodiment in certain combinations of elements, arrangements of parts and series of steps by which the aforesaid aspects, features and considerations and certain other aspects, features and considerations are attained, all with reference to the accompanying drawings and the scope of which will be more particularly pointed out and indicated in the appended claims.

BRIEF DESCRIPTION OF THE DRAWINGS

In the accompanying drawings in which are shown one of the various possible exemplary embodiments of the invention.

DESCRIPTION OF THE PREFERRED EMBODIMENTS

Figure 1:
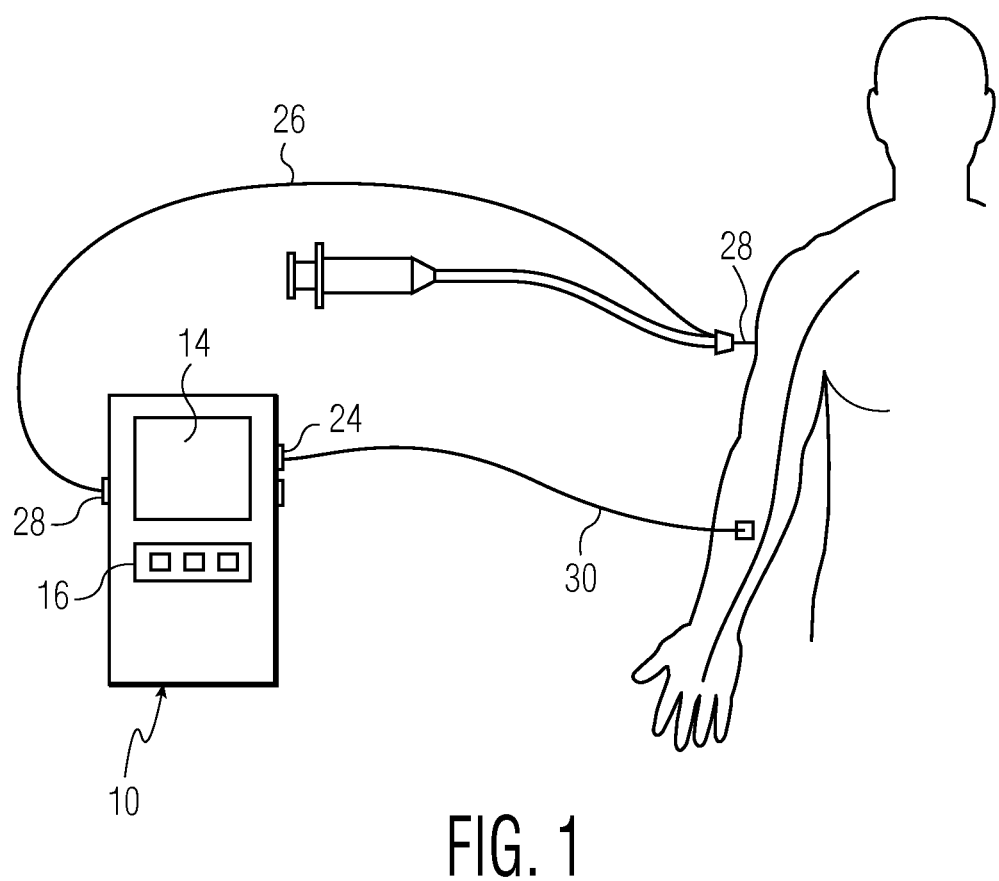
FIG. 1 is a schematized illustration of a typical application of the nerve stimulation system of the present invention as may be employed to position a nerve stimulator needle for locating a target median nerve.
Figure 2:
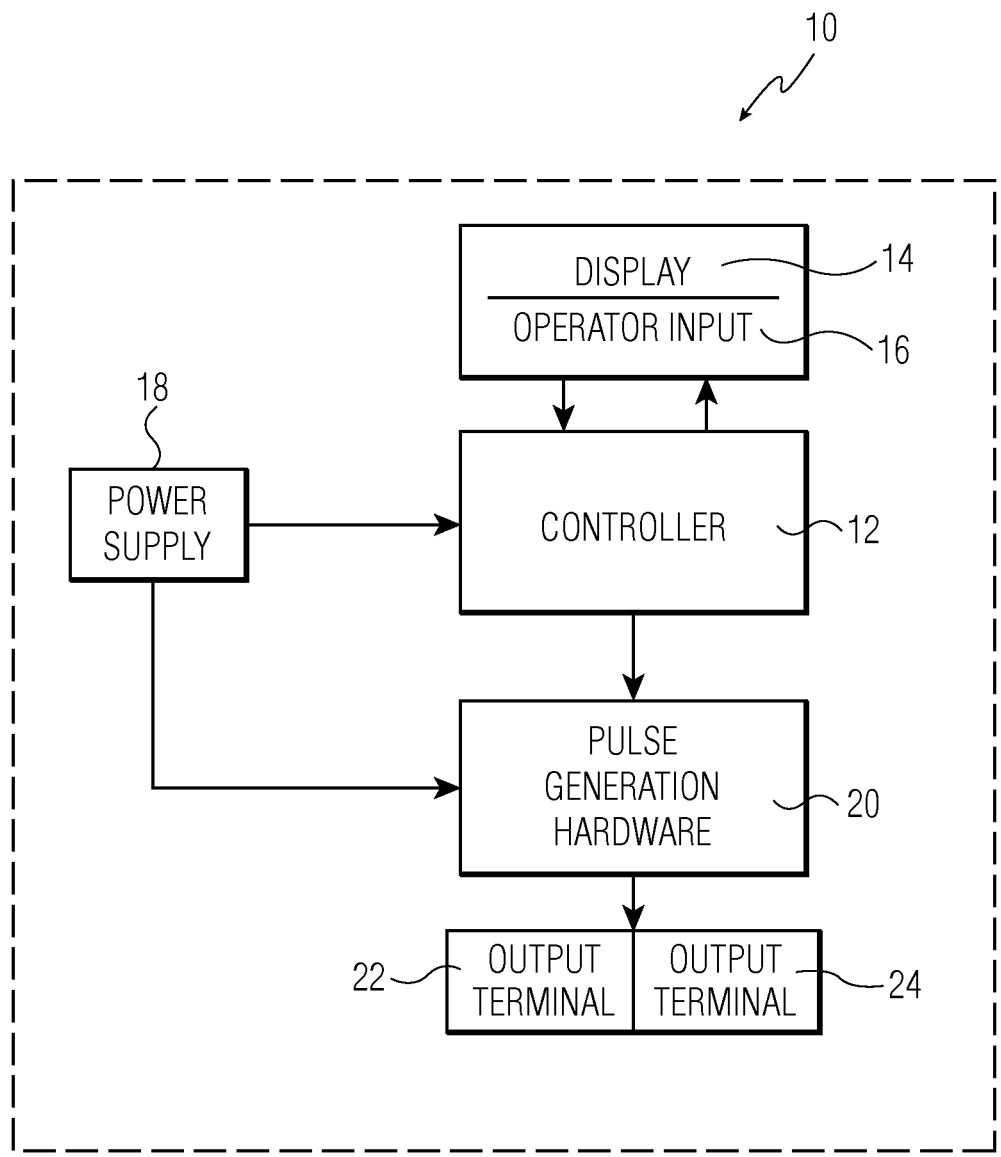
FIG. 2 is a schematized block diagram of components of the nerve stimulator system of the present invention and illustrating a controller coupled to pulse generation hardware for controlling the generation of a nerve stimulator output in accordance with the invention.

Referring now in detail to the drawings, the reference numeral 10 denotes generally a nerve stimulation system constructed in accordance with and embodying the invention. The system 10 includes a controller e.g. a microprocessor, which is programmed to vary one nerve stimulator output pulse charge component, such as pulse width or pulse current amplitude, as a predetermined function of the operator set incremental value of the other pulse charge component. A selected one of multiple functions may be employed as empirically determined for the specific target nerve or other anatomic parameters.

The controller 12 is coupled to input output devices such as an operator interface comprising a display 14 as well as operator inputs 16. The operator inputs 16 may comprise portions of a touch screen incorporated in the display 14 or may comprise keys, a membrane touch pad or other input devices such as employed in conventional nerve stimulators, e.g. a potentiometer, for setting program modes and for adjustment of variable parameters such as pulse current amplitude or pulse width.

A power supply 18 is employed to power the controller as well as the input/output devices 14, 16 and a pulse generator i.e. pulse generation hardware 20. The controller 12 generates a signal which is applied to the pulse generation hardware 20 for controlling the pulse train output of the pulse generation hardware. Depending upon the specific transfer function applicable to the specific procedure at hand, the controller 12 is programmed to vary, for example, pulse width as a specific function of the operator adjusted incrementally set value of pulse current amplitude, which value is set at the operator input 16. The operator input 16 is also employed to set the appropriate mode of operation of the controller, e.g. the specific programmed function, etc. The pulse generation hardware output is presented at a pair of output terminals 22, 24.

With reference now to FIG. 1, it will be appreciated that a lead 26 interconnects one of the output terminals, 22 for example, to an administration needle 28, while a return current path lead 30 interconnects the patient to the other output terminal 24.

With the nerve stimulation system 10 attached to the needle or cutaneous probe 28, the system 10 may be deployed for invasive electrical location of a nerve or nerves or for the percutaneous electrode guidance technique shown in U.S. Pat. No. 6,533,732, incorporated herein by reference, or for noninvasive transcutaneous location of a nerve or nerves. The system 10 may also be employed in conjunction with combined percutaneous/subcutaneous electrode guidance as described in U.S. Patent Publication No. 2004/0059247, incorporated herein by reference.

Among the several operating modes programmed in the controller 12 is conventional nerve stimulation as presently practiced. Such mode is selectable through the operator input 16 and permits the practitioner to incrementally increase or decrease the pulse current amplitude, while the output pulse train is maintained at a constant pulse width, e.g. 0.1 msec.

A further programmed operating mode which may be selected is the generation of an output pulse train having repeating cycles of three progressively smaller or progressively larger pulse width components, each separated by ⅓ of the waveform frequency, e.g. ⅓ sec. As with the first mode, the practitioner may incrementally increase or decrease the pulse current amplitude through actuation of the operator input 16, while the pulse widths of each of the pulse width components is maintained.

When employing this second operating mode, the practitioner will notice, at a distance from the target nerve, stimulation, e.g. contractions, responsive to the largest pulse width component at one second intervals. As the needle 28 is advanced towards the target nerve, the intermediate pulse width component will commence stimulation of the target nerve and the practitioner will notice two contractions, ⅓ of a second apart, separated by a dwell having a ⅓ second duration.

When the target nerve is proximate the needle tip, nerve contractions will be elicited from each of the pulse width components and will appear at the increased rate of 3 per second.

Deviations from the progressively increasing rate of contractions indicates that the stimulation needle 28 has diverted, that is, is traveling in a skew path. For example, if the contraction elicited by the intermediate width component appears and is then lost, the practitioner will become aware, at an intermediate depth of needle penetration, that adjustment of the needle path is necessary.

When set to a pulse charge attenuation mode by the operator input 16, the controller 12 actuates the pulse generation hardware 20 to generate a pulse train waveform output wherein one of the pulse charge components, i.e. pulse current amplitude or pulse width, varies as a function of the incrementally adjusted value of the other.

Figure 3:
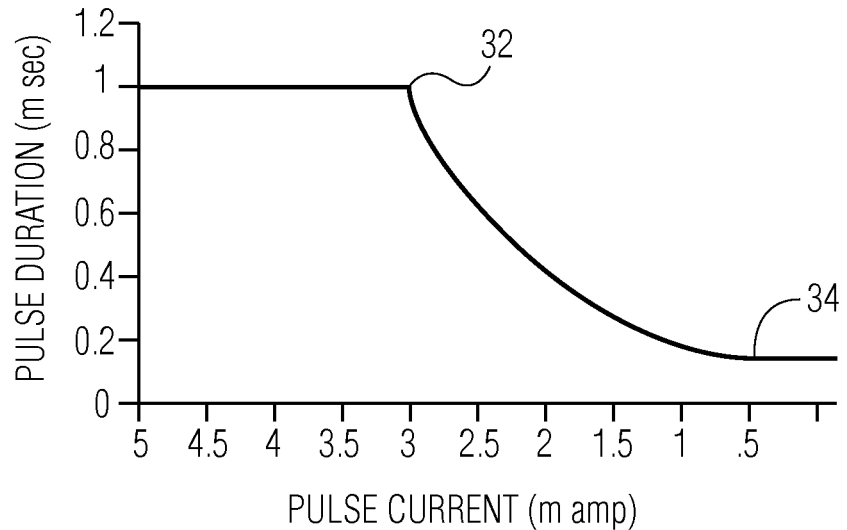
FIG. 3 is a graph representing nerve stimulator output pulse charge components and showing pulse width or pulse duration varying as a function of pulse current amplitude in accordance with the invention.
Figure 4:
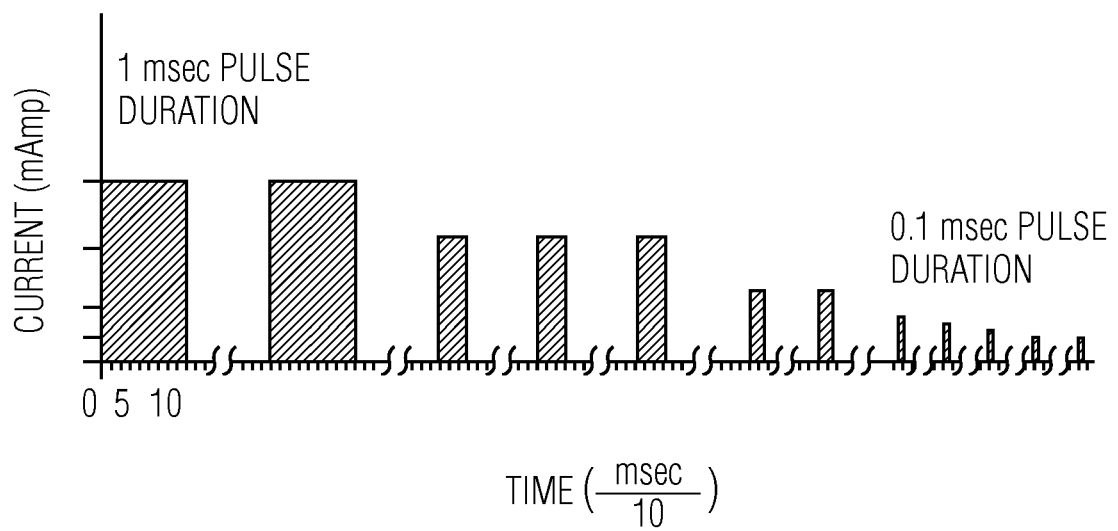
FIG. 4 is a bar graph representation of pulse width values varying as a function of pulse current amplitude, as depicted in FIG. 3.

Referring to the graphic representation depicted in FIG. 3, the pulse charge component values are set at, for example, 5 mAmp current amplitude and 1 msec pulse width for nerve stimulation at a distance from the target nerve. As the nerve stimulator needle 28 is advanced toward the target nerve, the practitioner incrementally reduces the pulse current amplitude so as to maintain uniform responsive contractions.

When the pulse current is reduced to a predetermined threshold value e.g. 3.0 mAmp, depicted as a point 32 in FIG. 3, the program enters an attenuation range wherein the pulse duration is reduced as a predetermined function of pulse amplitude, e.g. exponentially, until a minimum value of, for example, 0.1 msec at a pulse amplitude of 0.5 mAmp, depicted as a point 34 in FIG. 3, or below, at which the needle will be appropriately positioned. The attenuation range thus extends between the points 32 and 34. Further reduction of pulse amplitude will not result in variation of pulse width.

Thus, as the nerve is approached, the responsive contractions are elicited by smaller and smaller pulse charges while the ability to stimulate the nerve is maintained.

The preprogrammed functions can be based upon empirically collected data and are optimally set for maximal linearity or any other relationship which might prove to be efficient for yielding greater information, sensitivity, specificity or enhanced patient comfort. Optimally, a function is programmed which will linearly elicit motor contraction over a broad range of current level adjustments.

Alternately, the controller 12 could be programmed to change current amplitude as a function of the incrementally adjusted values of pulse width, which would change in a linear manner.

When employing a wave train output of square waves of constant pulse duration, the minimal current amplitude required to stimulate a nerve varies as a function of the inverse square of the distance from the stimulating electrode to the nerve.

As a result, when conventional nerve stimulation is employed, as the needle is advanced slowly to the nerve, it is typical to have the sudden appearance of a strong motor response.

Since the pulse width gradually changes as a function of the applied current amplitude, an exponential increase in pulse width as a function of pulse amplitude allows for a greater range in the ability to elicit a motor response at a distance from the nerve. Initial high pulse durations that are exponentially related to current amplitude compensate for the fact that the minimal current amplitude increases exponentially as a function of the distance from the nerve. Thus, a more linear relationship between minimal current amplitude and the distance from the nerve is achieved. The practitioner is thus able to observe gradual changes in the ability to stimulate and observe contractions, for example, at a distance from the nerve, without sacrificing specificity of final nerve location with the needle tip.

Various functional relationships of the change of pulse width as a function of pulse current amplitude or pulse current amplitude as a function of pulse width can be empirically determined for different target nerves or plexuses of nerves. For example, with respect to specific nerves or deep nerves, high initial pulse widths would be more appropriate than for superficial nerves and the functional relationship would thus require a higher level exponential or other function of amplitude. It is anticipated that specific functions can be derived for specific nerves, types of nerves or nerve groups and a practitioner would select the appropriate program for the specific target nerve at the operator input 16.

As previously mentioned, the functional relationship between pulse width and pulse current amplitude for a specific nerve may be empirically determined by plotting. For example, a needle may be anatomically positioned for locating the target nerve by employing the electrode guidance devices and techniques disclosed in U.S. Pat. No. 6,533,732 or U.S. Patent Publication No. 2004/0059247.

Upon subcutaneous penetration of the needle, the current amplitude is reduced in a stepped manor to elicit stimulation of the target nerve with maximum pulse width. The needle is then advanced an incremental linear distance, e.g. 2 mm and the current amplitude is incrementally reduced, e.g. from 5 mAmp to 4.5 mAmp, etc. with substantially the same nerve stimulation level as initially noted.

The incremental advancement of the needle and reduction in pulse amplitude continues until reaching a certain needle penetration depth correlated to the pulse amplitude, e.g. 3.0 mAmp to 2.5 mAmp (the point 32 on the FIG. 3 graph), after which it becomes necessary to reduce the pulse width in order to maintain the stimulation level.

The incremental linear advancement of the needle combined with incremental reduction in pulse amplitude and reduction of the pulse width level necessary to maintain the nerve stimulation level continues until a point is reached, for example, wherein the pulse amplitude is approximately 0.5 mAmp (the point 34 on the FIG. 3 graph), for example, after which further reduction in pulse width is no longer necessary and the needle tip is appropriately positioned.

Transfer functions of pulse amplitude versus pulse width which correlates to the plotted values for each of a variety of nerves or plexuses of nerves is then generated and programmed into the controller 12.

A further mode of operation which may be selected at the operator input 16 is the generation of an output pulse train having repeating cycles of three progressively smaller or progressively larger pulse width components, each separated by ⅓ of the waveform frequency, e.g. ⅓ sec., combined with pulse charge attenuation.

Figure 5:
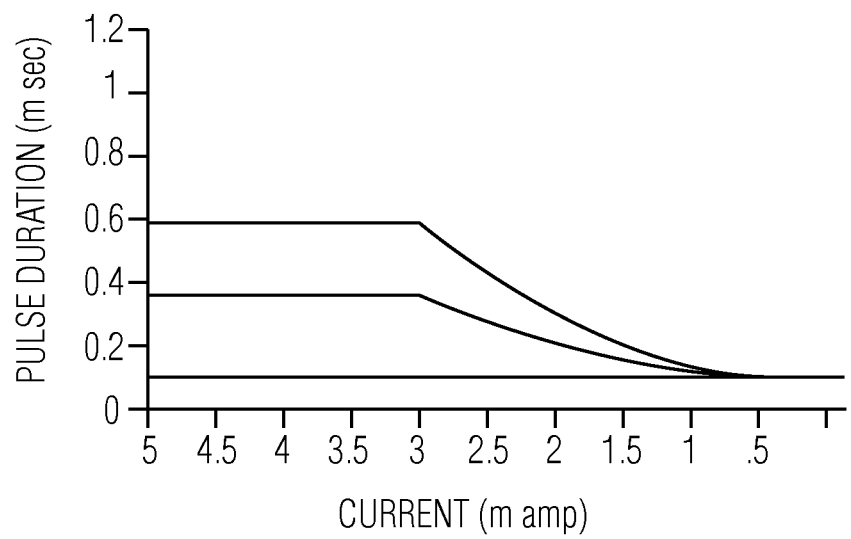
FIG. 5 is a graphic representation of a nerve stimulator output pulse charge components in accordance with the invention wherein the pulse train includes cycles of different pulse width components with each pulse width component varying as a function of applied current amplitude.
Figure 6:
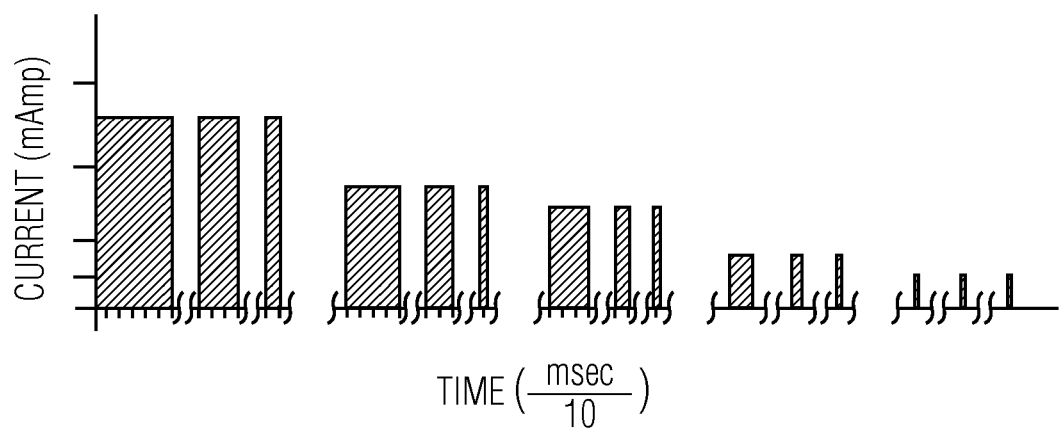
FIG. 6 is a bar graph representation of pulse width values of each of the three pulse width components illustrated in FIG. 5 varying as a function of applied current amplitude.

With reference to FIG. 5, a plot of pulse charge values for each of three pulse width components is depicted. A largest pulse width component is indicated at an initial pulse width of 0.6 msec, an intermediate pulse width component with an initial pulse width of 0.4 msec and a smallest pulse width component having an initial pulse width of 0.6 msec.

As previously mentioned, employment of progressively larger or progressively smaller pulse width components facilitates guidance of the needle by examining the changes in the rate of contractions or the rate of other indications of nerve stimulation.

Referring again to FIG. 5, it should be noted that the pulse charge values for each of the pulse width components are initially set, for example, at 5 mAmp pulse current amplitude. As the practitioner advances the needle toward the target nerve, the practitioner incrementally reduces, in a linear fashion, the pulse current amplitude so as to maintain nerve stimulation.

When the pulse current is reduced beyond a predetermined threshold value such as 3.0 mAmp or 2.5 mAmp, the controller 12 reduces the pulse width of each of the pulse width components as a predetermined function of the applied pulse amplitude until a uniform minimum pulse width of, for example 0.1 msec is obtained at a pulse amplitude of 0.5 mAmp or below at which the needle will be appropriately positioned.

Thus it will be seen that there is provided a nerve stimulation system with programmed pulse charge attenuation which achieves the various aspects, features and considerations of the present invention and which is well adapted to meet the conditions of practical usage.

Since various possible embodiments might be made of the present invention and since various changes might be made in the exemplary embodiment set forth herein without departing from the spirit of the invention, it is to be understood that all matter herein described or shown in the accompanying drawings is to be interpreted as illustrative and not in a limiting sense.

Having thus described the invention, there is claimed as new and desired to be secured by Letters Patent:

1. A nerve stimulation system configured to position an administration needle proximate a target nerve, the system comprising:
   an operator interface including an operator input;
   a pulse generator configured to generate a pulse output waveform at an output terminal, wherein the pulse output waveform comprises pulses, each pulse having a pulse charge comprising a function of a first variable parameter and a second variable parameter, the variable parameters comprising pulse current amplitude and pulse width;
   a controller operatively connected to the pulse generator and to the operator interface; and
   an administration needle configured for administration of an anesthetic, the administration needle operatively connected to the output terminal;
   wherein the operator input is configured to input signals to the controller and incrementally reduce the value of the first variable parameter and the controller is programmed to reduce the value of the second variable parameter as a function of incrementally set values of the first variable parameter.

2. A nerve stimulation system configured to position an administration needle proximate a target nerve as constructed in accordance with claim 1, wherein the function is exponential.

3. A nerve stimulation system configured to position an administration needle proximate a target nerve as constructed in accordance with claim 2, wherein the first variable parameter comprises pulse current amplitude and the second variable parameter comprises pulse width.

4. A nerve stimulation system configured to position an administration needle proximate a target nerve as constructed in accordance with claim 1, wherein the first variable parameter comprises pulse current amplitude and the second variable parameter comprises pulse width.

5. A nerve stimulation system configured to position an administration needle proximate a target nerve as constructed in accordance with claim 4, wherein the controller maintains constant pulse width over an initial range of incrementally set pulse current amplitude values and thereafter attenuates pulse width over an attenuation range of reduced incrementally set pulse current amplitude values.

6. A nerve stimulation system configured to position an administration needle proximate a target nerve as constructed in accordance with claim 4, wherein the controller maintains constant pulse width when current amplitude values are reduced below the attenuation range.

7. A nerve stimulation system configured to position an administration needle proximate a target nerve as constructed in accordance with claim 4, wherein the pulses are configured in a pulse train having repeating cycles of three different pulse width components separated by ⅓ of the waveform frequency.

8. A nerve stimulation system configured to position an administration needle proximate a target nerve as constructed in accordance with claim 7, wherein the controller is programmed to simultaneously reduce the value of the pulse width parameter of each pulse width component as a function of an incrementally reduced value of the pulse amplitude parameter.

9. A nerve stimulation system configured to position an administration needle proximate a target nerve as constructed in accordance with claim 1, wherein the function has been empirically derived.

10. A nerve stimulation system configured to position an administration needle proximate a target nerve as constructed in accordance with claim 1, the controller being programmed with multiple modes of operation.

11. A nerve stimulation system configured to position an administration needle proximate a target nerve as constructed in accordance with claim 10, wherein the pulse generator generates a pulse output waveform comprising repeating cycles of three different pulse width components separated by ⅓ of the waveform frequency and the operator input is configured to input a signal to the controller to incrementally vary the pulse current amplitude of each of the pulse width components.

12. A method of programming the controller of a nerve stimulation system constructed in accordance with claim 1, wherein the target nerve is situate in a subject, the method comprising the steps of:
   i) introducing the administration needle into the subject at a location anatomically positioned for locating the target nerve to elicit stimulation of the target nerve,
   ii) incrementally advancing the administration needle toward the target nerve while incrementally reducing the pulse current amplitude,
   iii) reducing the pulse width to maintain stimulation while performing step ii),
   iv) observing correlated values of pulse current amplitude and pulse width for maintaining stimulation while performing steps ii) and iii), and
   v) programming the controller with a transfer function of pulse current amplitude versus pulse width which correlates to the observed correlated values.

13. A nerve stimulation system configured to position an administration needle proximate a target nerve as constructed in accordance with claim 1, wherein the first variable parameter comprises pulse width and the second variable parameter comprises pulse current amplitude.

14. A nerve stimulation system configured to position an administration needle proximate a target nerve as constructed in accordance with claim 13, wherein the controller is configured to attenuate pulse current amplitude over an attenuation range of reduced incrementally set pulse width values.

15. A method of administering regional anesthesia to a subject utilizing a nerve stimulation system constructed in accordance with claim 1, the target nerve being situate in the subject, the method comprising the steps of:
 a) subcutaneously penetrating the subject with the administration needle,
 b) noting muscular contractions of the subject responsive to stimulation of the target nerve,
 c) advancing the administration needle toward the target nerve,
 d) engaging the operator input to incrementally reduce the first variable parameter and, in response the controller reducing the value of the second variable parameter to maintain muscular contractions,
 e) terminating step c) and step d) when a minimum value level of the first variable parameter is reached while maintaining muscular contractions, and
 f) administering an anesthetic through the administration needle.

16. A nerve stimulation system configured to position an administration needle proximate a target nerve as constructed in accordance with claim 1, wherein the target nerve is situate in a subject, the pulse generator is configured to generate a pulse output waveform at a pair of output terminals, the administration needle is operatively connected to a first of the pair of output terminals, the administration needle is configured to be introduced into the subject at a location anatomically positioned for locating the target nerve, and the system further including a return current path lead operatively connected between the subject and a second of the pair of output terminals.

17. A nerve stimulation system configured to administer regional anesthesia proximate a target nerve, the stimulation system comprising:
 an operator interface;
 a pulse generator configured to generate a pulse output waveform at an output terminal;
 a controller operatively connected to the pulse generator and the operator interface; and
 an administration needle configured to administer an anesthetic, the administration needle operatively connected to the output terminal;
 wherein the pulse output waveform comprises repeating cycles of three different pulse width components of equal pulse current amplitude separated by ⅓ of the waveform frequency and the operator interface is configured to input a signal to the controller to simultaneously vary the pulse current amplitude of each pulse width component.

18. A nerve stimulation system configured to administer regional anesthesia proximate a target nerve as constructed in accordance with claim 17, wherein the three different pulse width components comprise a first width component followed by two progressively smaller width components.

19. A method of programming a controller of a nerve stimulation system having a pulse generator which generates a pulse waveform output and an operator interface, the pulse waveform comprising pulses, each pulse having a pulse current amplitude and a pulse width, the controller being operatively connected to the pulse generator and to the operator interface, the method comprising the steps of:
 a) operatively connecting an administration needle to the pulse generator,
 b) introducing the administration needle into a subject at a location anatomically positioned for locating a target nerve to elicit stimulation of the target nerve,
 c) advancing the administration needle toward the target nerve while incrementally reducing the pulse current amplitude,
 d) reducing the pulse width to maintain stimulation while performing step c),
 e) observing and noting values of pulse current amplitude and pulse width necessary to maintain stimulation of the target nerve while performing steps c) and d), and
 f) programming the controller with a transfer function of pulse current amplitude versus pulse width which correlates to the noted values.

20. A method of programming a controller of a nerve stimulation needle in accordance with claim 19, wherein step c) is performed by linearly advancing the administration needle.

* * * * *